United States Patent
Lester et al.

(10) Patent No.: US 7,476,255 B2
(45) Date of Patent: Jan. 13, 2009

(54) SOFT TISSUE ATTACHMENT SYSTEM AND METHOD

(75) Inventors: Mark Lester, Warsaw, IN (US); Scott Wilson, New Orleans, LA (US)

(73) Assignee: DePuy Products, Inc., Warsaw, IN (US)

( * ) Notice: Subject to any disclaimer, the term of this patent is extended or adjusted under 35 U.S.C. 154(b) by 694 days.

(21) Appl. No.: 10/748,706

(22) Filed: Dec. 30, 2003

(65) Prior Publication Data

US 2005/0143834 A1    Jun. 30, 2005

(51) Int. Cl.
*A61F 2/36* (2006.01)
(52) U.S. Cl. .............. 623/23.15; 623/18.11; 623/23.26; 623/23.28
(58) Field of Classification Search .............. 623/16.11, 623/18.11, 19.11, 20.17, 22.11, 22.43, 22.46, 623/23.14, 23.15, 23.21, 23.28, 23.29, 23.3, 623/23.31, 23.35
See application file for complete search history.

(56) References Cited

U.S. PATENT DOCUMENTS

| 3,875,936 | A | | 4/1975 | Volz |
| 3,939,468 | A | * | 2/1976 | Mastin ........................ 367/22 |
| 3,973,277 | A | | 8/1976 | Semple et al. |
| 4,120,298 | A | | 10/1978 | Fixel |
| 4,236,512 | A | | 12/1980 | Aginsky |
| 4,889,110 | A | * | 12/1989 | Galline et al. ................. 606/69 |
| 5,004,475 | A | | 4/1991 | Vermeire et al. |
| 5,163,961 | A | * | 11/1992 | Harwin .................... 623/22.46 |
| 5,281,422 | A | | 1/1994 | Badylak et al. |
| 5,372,821 | A | | 12/1994 | Badylak et al. |
| 5,391,169 | A | | 2/1995 | McGuire |
| 5,445,833 | A | | 8/1995 | Badylak et al. |
| 5,573,784 | A | | 11/1996 | Badylak et al. |
| 5,665,088 | A | | 9/1997 | Gil et al. |
| 5,788,625 | A | | 8/1998 | Plouhar et al. |
| 5,797,916 | A | | 8/1998 | McDowell |
| 5,922,028 | A | | 7/1999 | Plouhar et al. |
| 5,941,881 | A | | 8/1999 | Barnes |
| 5,984,927 | A | | 11/1999 | Wenstrom, Jr. et al. |
| 6,008,431 | A | * | 12/1999 | Caldarise et al. ........... 623/23.3 |
| 6,176,880 | B1 | | 1/2001 | Plouhar et al. |
| 6,273,915 | B1 | | 8/2001 | Grimes |
| 6,338,734 | B1 | | 1/2002 | Burke et al. |
| 6,537,319 | B2 | | 3/2003 | Whelan |
| 2002/0022840 | A1 | | 2/2002 | Martello |
| 2002/0022889 | A1 | | 2/2002 | Chibrac et al. |

(Continued)

FOREIGN PATENT DOCUMENTS

EP    0 604 082    6/1994

(Continued)

*Primary Examiner*—Bruce E Snow
(74) *Attorney, Agent, or Firm*—Maginot, Moore & Beck

(57) ABSTRACT

A system and method is provided in which natural bone removed during a joint surgery is retained along with the natural attachment of the associated soft tissues. For instance, in a hip surgery, a portion of the greater trochanter is removed while retaining the soft tissue attachments. An implant and the bone portion are provided with mating features, such as a keystone configuration. The keystone configuration can include mating male and female dovetail configurations. The bone portion can be engaged to the mating feature of the implant to support the natural bone and its soft tissue attachment in an anatomically appropriate position.

12 Claims, 3 Drawing Sheets

U.S. PATENT DOCUMENTS

| | | |
|---|---|---|
| 2002/0133232 A1 | 9/2002 | Ricci et al. |
| 2002/0143333 A1 | 10/2002 | Hoffmann et al. |
| 2003/0013068 A1 | 1/2003 | Gittleman |
| 2003/0065390 A1 | 4/2003 | Justin et al. |

FOREIGN PATENT DOCUMENTS

| | | |
|---|---|---|
| EP | 0 729 732 | 9/1996 |
| EP | 0 605 581 | 12/2001 |
| EP | 0 986 331 | 8/2002 |
| EP | 1 260 181 | 11/2002 |
| FR | 2 810 232 | 12/2001 |
| WO | WO 96/40307 | 12/1996 |
| WO | WO 97/37613 | 10/1997 |

\* cited by examiner

SOFT TISSUE ATTACHMENT SYSTEM AND METHOD

BACKGROUND OF THE INVENTION

The present invention relates to orthopaedic implants and procedures in which a portion of bone is removed to which soft tissues, such as ligaments and tendons, are attached. In particular, the invention relates to systems and methods for maintaining the soft tissue attachment during an orthopaedic procedure.

Certain orthopaedic surgeries, such as hip surgeries, often require osteotomies of a portion of the femur to provide full access to the hip joint. In these procedures, a portion of the greater trochanter is removed. Following the surgery, the removed bone portion is replaced and secured in a number of ways. For instance, trochanter reattachment systems can include wiring, cables or clamps that are used to hold the removed portion to the retained bone long enough to promote healing through fusion.

In some orthopaedic procedures, a significant portion of a joint is replaced with a prosthesis. For instance, in some hip surgeries, the entire proximal portion of the femur is removed and replaced with the prosthesis. Since the attachment point for the soft tissue is removed with the bone, surgeons have turned to composite allograft-endoprosthesis constructs to provide a foundation for connection of the soft tissue to the implant. Usually, the soft tissue, such as tendons, are connection by sutures, so that the resulting connection is only as strong as the suture. The success of these types of reconstruction is historically low.

What is needed is a system and method that preserves as much of the natural attachment point for soft tissue as possible. An optimum approach would make use of as much of the natural bone as possible so that the attachment of the soft tissue to the bone is not compromised or replaced by a less secure attachment.

SUMMARY OF THE INVENTION

In view of these needs, the present invention contemplates a system and method in which the natural removed bone is retained, along with the natural attachment of the associated soft tissues. For instance, in a hip surgery, a portion of the greater trochanter is removed while retaining the soft tissue attachments. The present invention provides means for receiving that bone portion and connecting it to a proximal femoral implant, for instance.

In one embodiment of the invention, the implant and bone portion are provided with mating features, such as a keystone configuration. The keystone configuration can include mating male and female dovetail configurations. The bone portion can be engaged to the mating feature of the implant to support the natural bone and its soft tissue attachment in an anatomically appropriate position.

In a preferred embodiment, the keystone and dovetail features are angled inward so that the natural tensile forces exerted on the bone portion will tend to force the male/female features into tighter engagement. In another feature, the implant can include a bone ingrowth surface at the interface to the bone portion to enhance the fixation of the natural bone to the implant.

In certain embodiments, separate fixation elements are provided to ensure a tight connection between the bone portion and the implant. In one embodiment, one or more cables can encircle the bone portion to hold the portion in position without interfering with the soft tissue and soft tissue attachments. In another embodiment, a hinged claw scaffold can be provided that can be pivoted into engagement with the bone portion. The scaffold can include claws to penetrate the bone. The scaffold can also include plate portions through which bone screws are driven into the underlying bone. The scaffold can also be configured to integrate with cables encircling the bone portion.

In a method of the invention, the portion of a bone, such as the femur, is removed as necessary to accept a prosthesis or implant, such as a proximal femoral implant. Certain portions of the removed bone that include soft tissue attachment points can be removed separately, while retaining the attachment to the soft tissues. The removed portion of the bone can be engaged within a cutting jig that is configured to permit forming the mating feature in the cut surface of the removed bone. The mating feature cut into the bone is complementary to a mating feature defined in an exposed surface of the implant.

In accordance with this method, the prosthesis is implanted within the remaining natural bone, with the exposed surface in proper alignment to accept the removed bone. The mating feature of the removed bone is engaged to the mating feature on the implant, while the soft tissue remains attached to the natural removed bone. Additional mechanical fixation can be provided to ensure a firm connection between the removed bone and the prosthesis as the surgical site heals.

It is one important object of the invention to provide a system and method for removal of portions of a bone, while retaining other portions of the bone bearing soft tissue attachments. A further object is to provide means for conducting complex orthopaedic surgical procedures, such as joint arthroplasty, while preserving the natural soft tissue and soft tissue attachment points.

Other objects and particular benefits of the present invention will become apparent upon consideration of the following written description and accompanying figures.

DESCRIPTION OF THE PREFERRED EMBODIMENTS

Figure 1:
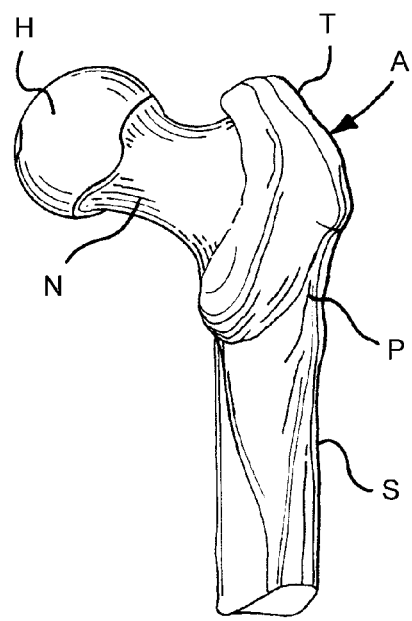
FIG. 1 shows a partial perspective view of a femur.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

For illustrative purposes, the preferred embodiments of the present invention will be explained in the context of an orthopaedic joint arthroplasty procedure for the hip joint involving the proximal portion of the femur, as depicted in FIG. 1. It is understood, of course, that the principles discussed herein can be applied to other joints and bones of the body. In the context of the present invention, one goal is to preserve the soft tissue attachments to portions of natural bone. It is further understood that features of the present invention can be utilized even where soft tissue attachments are not a concern.

As shown in FIG. 1, a bone, such as the femur, includes a shaft S terminating in a proximal portion P that is configured to form an articulating component of a joint, such as the hip joint. To that end, the proximal portion includes a neck N supporting a head H that provides the articulating surface. In the case of a femur, the head H is a ball joint component. Various soft tissues, such as flexor tissues, are connected to the bone at the proximal portion P, particularly at the greater trochanter T. The trochanter includes various soft tissue attachment points T for tendons associated with muscles of the hip joint, such as certain gluteal muscles.

Figure 2:
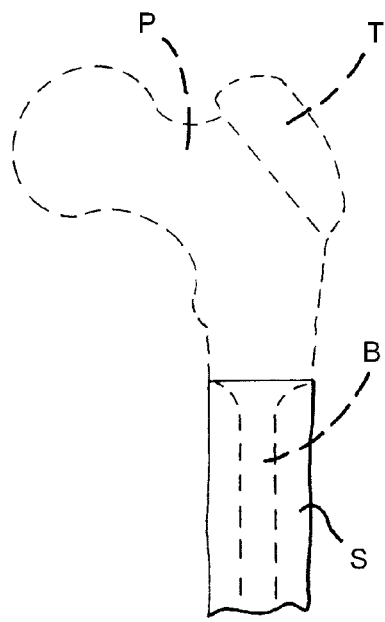
FIG. 2 shows a schematic view of the femur of FIG. 1 identifying resected bone portions in accordance with principles of the present invention.

In certain orthopaedic procedures, the proximal portion P of the femur is removed, as depicted by the dashed lines in FIG. 2. A bore B is formed in the bone shaft S to receive portions of an implant or prosthesis, such as the proximal prosthesis shown in FIG. 3. In a typical procedure, the trochanter T is removed with the proximal portion, and the soft tissue attachments severed. In some procedures, it is possible to integrate an allograft component with the prosthesis, and then to suture the soft tissues to the allograft component, thereby restoring the soft tissue attachment to the bone.

The prosthesis 10 can be similar to known designs for use in hip joint arthroplasty procedures. For instance, the prosthesis 10 can include a body 11 that is configured to approximate the removed proximal portion P of the femur. The body defines a neck 12 onto which a prosthetic articulating component of known design can be mounted. The prosthesis also includes a stem 13 that is implanted within the bore B to fix the prosthesis to the bone.

Figure 3:
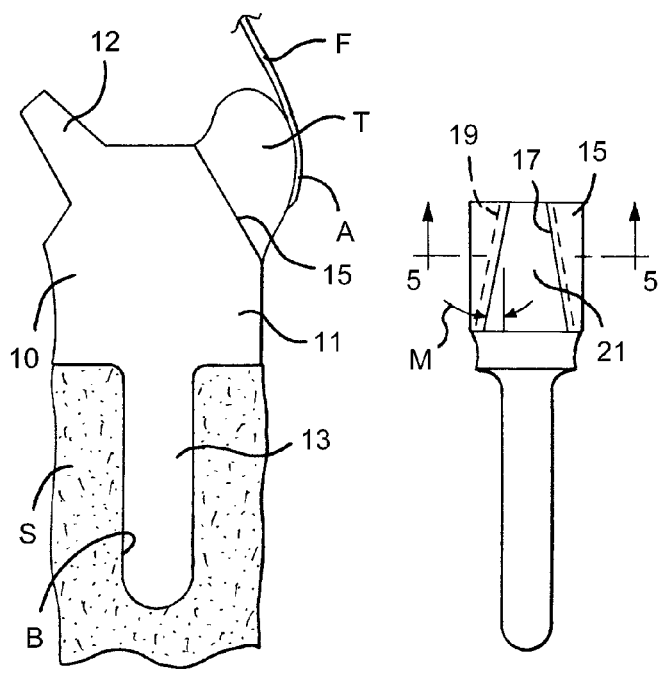
FIG. 3 shows a partial cutaway view of the femur of FIG. 2 with a proximal prosthesis implanted therein, the proximal prosthesis having a trochanter engaged thereto in accordance with principles of the present invention.

While prior hip joint prostheses include a body that emulates the shape of the trochanter, the present invention contemplates that the body 11 defines a mounting platform 15 that is arranged to coincide with the surface of the proximal portion P remaining after the trochanter T has been removed therefrom (see FIG. 2). This mounting platform 15 defines surface features for mating engagement with the removed portion of the trochanter T. As shown in FIG. 3, the attachment point A for certain flexor tissues F is maintained even as the trochanter portion T is engaged to the mounting platform.

Figure 4:
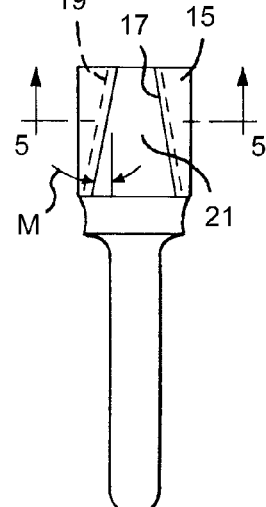
FIG. 4 shows a plan view of the proximal prosthesis of FIG. 3 with the trochanter removed to show a mounting platform in accordance with principles of the present invention.
Figure 5:
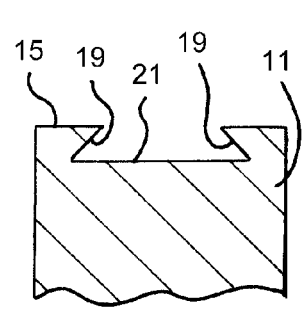
FIG. 5 shows a partial cross-section view of the mounting platform of FIG. 4 showing a keystone slot with dove-tail undercuts.

In one aspect of the invention, the mounting platform and the bone portion T define mechanical engagement or mating features that allow the bone portion to be engaged to the prosthesis 10 when the prosthesis is in its implanted position. As shown in FIGS. 4 and 5, the mounting platform defines a keystone slot 17 with a dovetail undercut 19 (best seen in FIG. 5). The slot includes a mating surface 21 that is in direct contact with the bone portion T.

Figure 6:
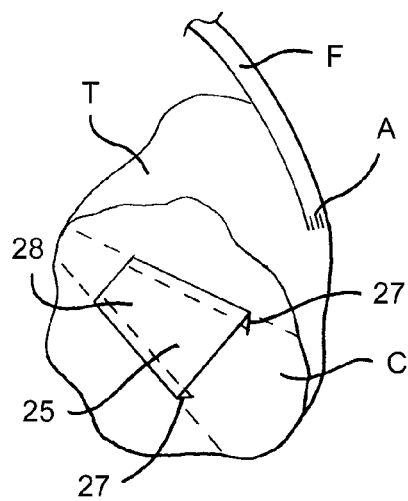
FIG. 6 shows the surface of the trochanter of FIG. 3 removed from the proximal prosthesis and prepared with a mating feature formed complementary to the mounting platform shown in FIG. 4 in accordance with principles of the present invention.
Figure 7:
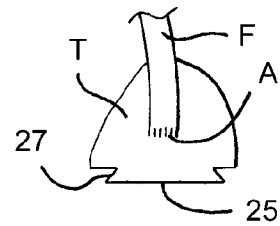
FIG. 7 shows a side view of the trochanter of FIG. 6.

The bone portion T is cut to define a mating feature 25, as illustrated in FIGS. 6 and 7. The mating feature includes a dovetail cut 27 at opposite sides of a mating surface 28. In the illustrated embodiment, the mating feature 25 is a male feature that projects from the cut surface C of the bone portion T and that is configured for interlocking engagement with a female feature 17 defined in the mounting platform 15 of the prosthesis. Alternatively, the male and female features can be swapped between the prosthesis and the bone portion, or a combination of male and female features can be defined on each component.

The dovetail elements, i.e., the undercut 19 and cut 27, are formed at a converging angle M. This converging feature provides a natural stop for insertion of the male mating feature 25 of the bone portion T into the female feature 17 of the prosthesis. In other words, once the prosthesis has been implanted, the bone portion T can be mounted to the prosthesis by sliding the mating feature 25 into the keystone slot 17. The bone portion is firmly engaged to the prosthesis when the angled walls of the dovetail cut 27 are flush with the complementary angled walls of the dovetail undercut 19. The converging angle M can be a Morse angle to enhance the engagement between the bone and the prosthesis.

As shown in FIG. 4, the keystone slot 17 can extend along the entire length of the mounting platform 15, as depicted in FIG. 4. Similarly, the mating feature 25 cut into the bone portion T can extend along the entire cut surface C, as represented by the dashed lines in FIG. 6. It is preferable that the extended mating features 17, 25 be fully complementary so that the male feature resides entirely and firmly within the female feature when the bone portion T is finally mounted to the prosthesis 10.

In the present embodiment, the fixation between the prosthesis and the bone portion is accomplished by the mating features 17 and 25. The mating surface 21 of the prosthesis contacts the mating surface 25 of the bone portion T. Preferably, the prosthesis mating surface 21 includes a bone ingrowth feature to permit bone ingrowth from the bone portion T into the prosthesis. The bone ingrowth feature can include a porous surface that can be filled with a bone growth promoting or enhancing material, such as bone morphogenic protein.

Figure 8:
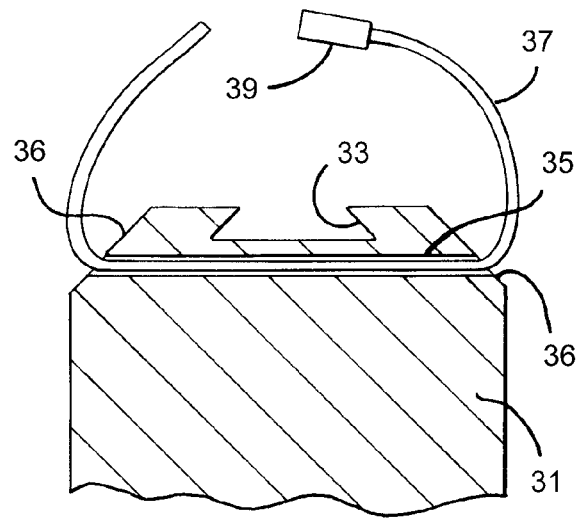
FIG. 8 shows a partial cross-sectional view of an alternative embodiment of a prosthesis that includes a keystone slot for mechanically mating with a prepared surface feature of a trochanter, the prosthesis including a bore for receiving a wire or cable used to provide additional mechanical fixation of a trochanter to the prosthesis in accordance with principles of the present invention.

In some instances, additional mechanical fixation may be desirable. In these cases, one embodiment of the invention contemplates the use of one or more cables that encircle the bone portion, in the nature of a cerclage device. Thus, as shown in FIG. 8, a prosthesis body 31 can be provided with a keystone slot 33, configured as described above. The body can define angled surfaces 36 on opposite sides of the keystone slot 33. A bore 35 passes through the body beneath the slot 33, as depicted in FIG. 8, opening at each of the angled surfaces 36. The bore is sized to receive a cable or wire 37 passing therethrough. One end of the cable 37 can carry a crimp 39 that can be crimped onto the opposite free end of the cable when it encircles the bone portion T. The cable can be tightened in a conventional manner, such as the manner in which a cerclage wire is tightened. The crimp 39 can also be of known design to firmly and permanently connect the ends of the cable. The cable 37 thus adds an additional mechanical fixation to hold the bone portion T to the prosthesis body 31.

Figure 9:
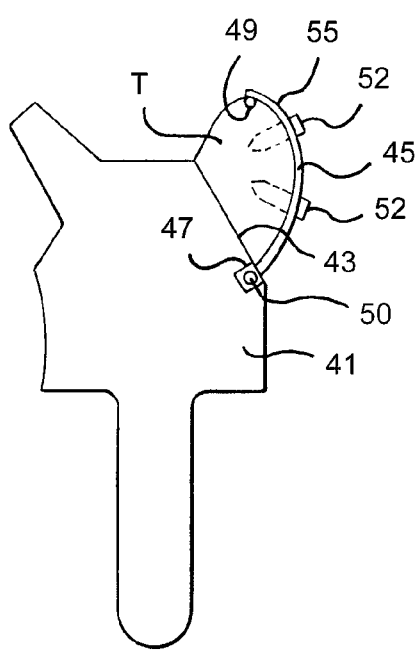
FIG. 9 shows a front plan view of an alternative embodiment of a prosthesis that may include a keystone slot for mechanically mating with a prepared surface feature of a trochanter, the prosthesis further including a slot for receiving an axle of a scaffold used to provide additional mechanical fixation of a trochanter to the prosthesis in accordance with principles of the present invention.
Figure 10:
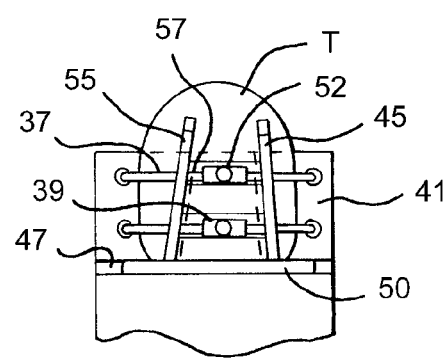
FIG. 10 shows a side plan view of an alternative embodiment of a scaffold incorporating cross bars to allow the use of bone screws to provide additional mechanical fixation of a trochanter to the prosthesis in accordance with principles of the present invention.

An alternative mechanical fastener is depicted in FIGS. 9-10. In this embodiment, a prosthesis body 41 defines a mounting platform 43 on which the bone portion T is mounted. The platform 43 can define a mating feature, such as the keystone slot 17 described above, to engage a corresponding mating feature on the bone portion, such as the dovetail feature 25. A scaffold 45 is mounted to the platform 43. In a specific embodiment, the platform defines a slot 47 for receiving an axle 50 of the scaffold. The slot and axle can be configured to permit pivoting of the scaffold from a position clear of the mounting platform 43, to permit mounting of the bone portion T thereon, to a position engaging the bone portion, as shown in FIG. 9.

The scaffold 45 includes at least two arms 55 that are configured to generally conform to the profile of the bone portion T. The arms 55 can include several claws 49 configured to penetrate at least the cortical layer of the bone portion T. The claws 49 are shown at the tip of the arms 55 in FIG. 9, but could be situated at different locations along the scaffold. The claws 49 provide means for engaging the scaffold to the bone portion to hold the portion in position on the prosthesis.

In an alternative embodiment, the scaffold 45 can include cross bars 57 spanning between the arms 55, as can be seen best in FIG. 10. The cross bars 57 provide a support surface for bone screws 52 passing through the cross bars into the underlying bone, as shown in FIG. 9. The bone screws 52 can be used in addition to or in lieu of the claws 49 described above. While only two bone screws are illustrated in the FIGS. 9-10, fewer or greater numbers of screws can be utilized. In addition, as shown in FIG. 9, the screws are sized to penetrate only part way into the bone portion T. Alternatively, the screws can be sized to pass entirely through the bone portion and engage a corresponding screw bore (not shown) formed in the mounting platform 43 of the prosthesis body 41.

As a further alternative, the cable system shown in FIG. 8 can be integrated with the scaffold 45 of FIGS. 9-10. In this alternative, the cable crimps 39 can be configured to include a bore (not shown) through which the bone screws 52 can pass. With this feature, the cable crimps can be connected to the scaffold to solidly hold the bone portion T to the prosthesis.

Figure 11:
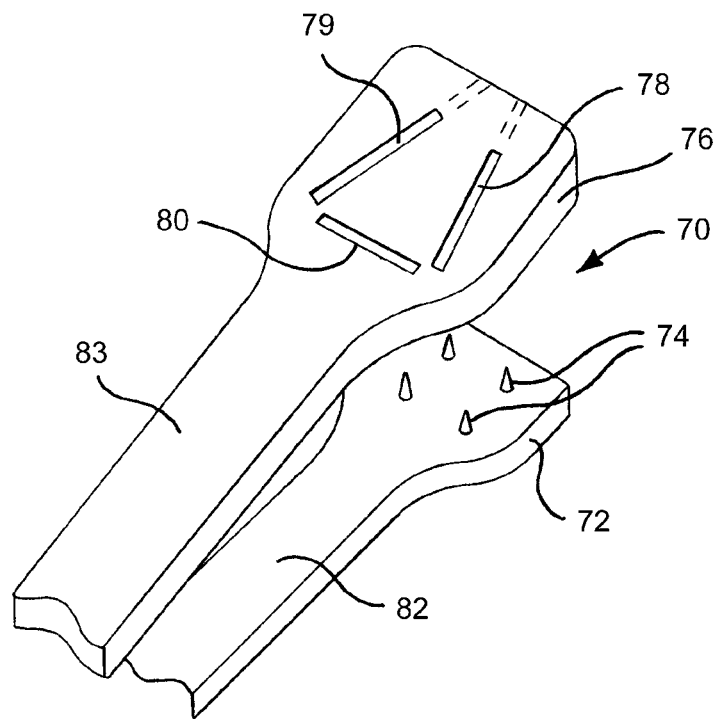
FIG. 11 shows a perspective view of a system including a cutting jig for preparing a removed bone portion to mate with a feature on a prosthesis in accordance with principles of the present invention.

The present invention also contemplates a system for preparing the removed bone portion T to add the mating feature 25. Thus, a cutting jig 70 can be provided as shown in FIG. 11. The jig includes two arms 82, 83 to clamp the bone portion therebetween. Both arms can be provided with spikes 74 to penetrate and grip the bone portion. The arm 82 defines a support base 72 to hold the proximal portion of the bone with the cut surface C (FIG. 6) facing a guide plate 76 carried by the opposite arm 83. The support base 72 can be shaped to conform to the profile of the bone portion.

Figure 12:
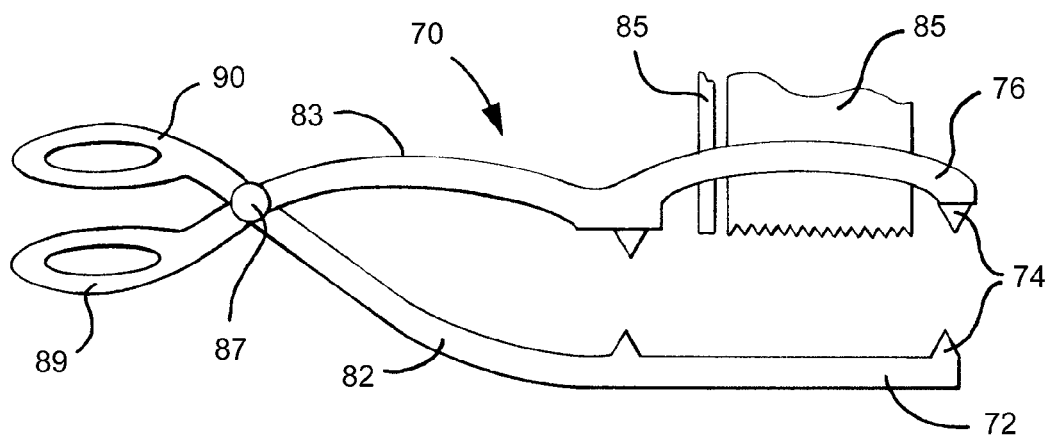
FIG. 12 shows a cutting tool used with slots in the cutting jig of FIG. 11 to create mating features on the removed bone portion.

The guide plate 76 defines a number of slots 78 that act as guides for saw blades, such as the blades 85 shown in FIG. 12. The slots are arranged as necessary to create the dovetail cuts 27 in the cut surface C of the bone. In the even that the dovetail cuts extend along the entire length of the bone portion, the slots 79 can be extended accordingly, as indicated by the dashed lines in FIG. 11.

In one embodiment, the cutting jig 70 is in the form of a manual scissors-type tool. Thus, the two arms can be connected at a pivot 87, as shown in FIG. 12, and can include grippable handles 89, 90. The cutting jig can thus be manipulated by the surgeon with one hand, while the cutting blades 85 are manipulated with the other hand. Of course, it is understood that the cutting jig 70 is not the only way that the bone portion can be fashioned with the mating feature 25. Any other technique for making the necessary cuts are contemplated, provided these cuts can be in situ made with the bone portion T attached to the soft tissues F.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for repair of a joint comprising the steps of:
   removing a portion of a bone having natural soft tissue attached thereto;
   implanting an implant within the remaining bone leaving an exposed surface of the implant;
   preparing a surface of the removed portion of bone to provide the surface with a surface feature to mechanically interlock with a complementary feature defined on the exposed surface of the implant; and
   mechanically engaging the surface feature of the removed portion of bone with the complementary feature of the implant when the implant is within the remaining bone while the natural soft tissue is still attached to the removed portion of bone such that the complementary feature of the implant does not extend completely through the removed portion of bone.

2. The method for repair of a joint according to claim 1, wherein:
   the complementary feature of the implant includes a female feature; and the step of preparing a surface includes defining a male surface feature on the removed portion of bone.

3. The method for repair of a joint according to claim 1, wherein the surface feature and the complementary feature define a dovetail joint.

4. The method for repair of a joint according to claim 1, wherein:
   the natural soft tissue is a ligament or a tendon; and
   the surface feature and complementary feature are configured to maintain the ligament or tendon in tension when the removed portion of bone is mechanically engaged to the implant.

5. The method for repair of a joint according to claim 4, wherein the surface feature and the complementary feature define opposing faces that diverge away from the intact attachment point of the ligament or tendon.

6. The method for repair of a joint according to claim 5, wherein the surface feature and the complementary feature define a dovetail joint.

7. The method for repair of a joint according to claim 1, further comprising the step of introducing bone cement between the removed portion of bone and the exposed surface implant.

8. The method for repair of a joint according to claim 1, further comprising the step of providing the exposed surface of the implant with a surface configured to promote bone tissue ingrowth.

9. The method for repair of a joint according to claim 1, wherein the joint is a hip joint, the removed portion of bone is the trochanter and the remaining bone is the remainder of the femur.

10. The method for repair of a joint according to claim 1, further comprising the step of fixing the removed portion of bone to the implant using a mechanical fastener.

11. The method for repair of a joint according to claim 10, wherein the mechanical fastener includes at least one screw configured to pass through the removed portion of bone and engage the implant.

12. The method for repair of a joint according to claim 10, wherein the mechanical fastener includes at least one cerclage wire configured to encircle at least a portion of the removed portion of bone and engage the prosthesis.

* * * * *